(12) United States Patent
Cho et al.

(10) Patent No.: US 8,952,209 B2
(45) Date of Patent: Feb. 10, 2015

(54) METHOD AND APPARATUS FOR CONTINUOUSLY PRODUCING 1,1,1,2,3-PENTAFLUOROPROPANE WITH HIGH YIELD

(71) Applicant: Foosung Co., Ltd., Hwaseong-si, Gyeonggi-do (KR)

(72) Inventors: ook jae Cho, Ulsan (KR); Jae Kug Ryu, Ulsan (KR); Bong Seok Kim, Ulsan (KR); Donghyun Kim, Ulsan (KR); Byounghun Park, Ulsan (KR); su jin Park, Ulsan (KR); Jin-A Jung, Ulsan (KR); Daewoo Kim, Seoul (KR)

(73) Assignee: Foosung Co., Ltd., Hwaseong-si, Gyeonggi-do (KR)

( * ) Notice: Subject to any disclaimer, the term of this patent is extended or adjusted under 35 U.S.C. 154(b) by 6 days.

(21) Appl. No.: 13/802,123

(22) Filed: Mar. 13, 2013

(65) Prior Publication Data
US 2014/0135538 A1   May 15, 2014

(30) Foreign Application Priority Data

Nov. 14, 2012   (KR) .................... 10-2012-0128695

(51) Int. Cl.

| | | |
|---|---|---|
| C07C 17/04 | (2006.01) | |
| C07C 19/08 | (2006.01) | |
| B01J 19/20 | (2006.01) | |
| B01J 27/06 | (2006.01) | |
| B01J 27/28 | (2006.01) | |
| B01J 8/10 | (2006.01) | |
| B01J 8/00 | (2006.01) | |

(52) U.S. Cl.
CPC .................. *C07C 17/04* (2013.01); *B01J 19/20* (2013.01); *B01J 27/06* (2013.01); *B01J 27/28* (2013.01); *B01J 8/10* (2013.01); *B01J 8/0045* (2013.01); *B01J 2208/00858* (2013.01)
USPC ........... 570/246; 570/175; 570/247; 570/253; 570/254

(58) Field of Classification Search
None
See application file for complete search history.

(56) References Cited

U.S. PATENT DOCUMENTS 2,589,862 A * 3/1952 Putney .......................... 208/155
2,759,026 A * 8/1956 McCleary ..................... 570/123
(Continued)

FOREIGN PATENT DOCUMENTS

DE    4335179 A1 *  4/1995
RU    2041194 C1 *  8/1995

OTHER PUBLICATIONS

RU 2041194 C1, Aug. 1995 (English translation).*
(Continued)

*Primary Examiner* — Jafar Parsa
*Assistant Examiner* — Medhanit Bahta
(74) *Attorney, Agent, or Firm* — Nixon Peabody LLP; Joseph Bach, Esq.

(57) ABSTRACT

A method and apparatus for method of continuously producing 1,1,1,2,3-pentafluoropropane with high yield is provided. The method includes (a) bringing a $CoF_3$-containing cobalt fluoride in a reactor into contact with 3,3,3-trifluoropropene to produce a $CoF_2$-containing cobalt fluoride and 1,1,1,2,3-pentafluoropropane, (b) transferring the $CoF_2$-containing cobalt fluoride in the reactor to a regenerator and bringing the transferred $CoF_2$-containing cobalt fluoride into contact with fluorine gas to regenerate a $CoF_3$-containing cobalt fluoride, and (c) transferring the $CoF_3$-containing cobalt fluoride in the regenerator to the reactor and employing the transferred $CoF_3$-containing cobalt fluoride in Operation (a). Accordingly, the 1,1,1,2,3-pentafluoropropane can be continuously produced with high yield from the 3,3,3-trifluoropropene using a cobalt fluoride ($CoF_2/CoF_3$) as a fluid catalyst, thereby improving the reaction stability and readily adjusting the optimum conversion rate and selectivity.

11 Claims, 2 Drawing Sheets

(56) References Cited

U.S. PATENT DOCUMENTS 2,827,502 A * 3/1958 Loeser et al. ................. 570/203
6,162,955 A * 12/2000 Na et al. ........................ 570/123
7,674,939 B2 * 3/2010 Mukhopadhyay et al. ... 570/156
8,624,067 B2 1/2014 Nose et al.

OTHER PUBLICATIONS

DE 4335179 A1, Apr. 1995 (English translation).*

* cited by examiner

METHOD AND APPARATUS FOR CONTINUOUSLY PRODUCING 1,1,1,2,3-PENTAFLUOROPROPANE WITH HIGH YIELD

CLAIM FOR PRIORITY

This application claims priority to Korean Patent Application No. 2012-0128695 filed on Nov. 14, 2012 in the Korean Intellectual Property Office (KIPO), the entire contents of which are hereby incorporated by reference.

BACKGROUND

1. Technical Field

Example embodiments of the present invention relate in general to the field of production of 1,1,1,2,3-pentafluoropropane, and, more specifically, to a method and apparatus for continuously producing 1,1,1,2,3-pentafluoropropane with high yield.

2. Related Art 1,1,1,2,3-pentafluoropropane ($CF_3CHFCH_2F$, HFC-245eb) is an intermediate useful in manufacture of 2,3,3,3-tetrafluoropropene ($CF_3CF=CH_2$, HFO-1234yf), which is effectively used as an alternative refrigerant of chlorofluorocarbon refrigerants, as represented by the following Scheme 1.

Scheme 1

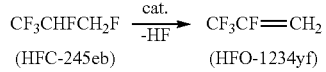

A method which includes sequentially performing hydrogenation, dehydrofluorination and hydrogenation of hexafluoropropene (HFP, $CF_3CF=CF_2$), as represented by the following Scheme 2, is known in the art as the method of producing HFC-245eb.

Scheme 2

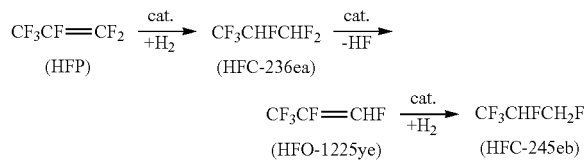

However, the method of producing HFO-1234yf as represented by Schemes 1 and 2 has problems in that a raw material, HFP, is relatively expensive, and is a complicated process which is composed of four operations including two hydrogenations and two dehydrofluorinations, which leads to relatively low industrial competitiveness.

A method of producing HFO-1234yf without producing HFC-245eb as an intermediate is a process using 1,1,1,3-tetrachloropropane ($CCl_3CH_2CH_2Cl$, HCC-250fb) as a raw material. HCC-250fb is produced through a reaction between carbon tetrachloride ($CCl_4$) and ethylene ($CH_2=CH_2$) as represented by the following Scheme 3. Here, the carbon tetrachloride and the ethylene are relatively inexpensive and can be readily supplied on a commercial scale.

Scheme 3

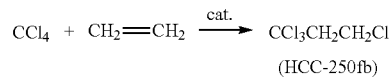

To produce HFO-1234yf using the HCC-250fb as a starting material, it is necessary to substitute one hydrogen atom bound to a central carbon atom with a halogen atom (F, Cl, Br, or I). In this regard, two methods are known in the related art.

(1) A method of substituting a hydrogen atom bound to carbon in the center of the molecule with a halogen atom before fluorination:

In this method, first, dehydrochlorination, chlorination and dehydrochlorination of HCC-250fb are sequentially carried out to produce 1,1,2,3-tetrachloropropene ($CCl_2=CClCH_2Cl$, HCO-1230xa) in which a hydrogen atom of the carbon in the center of the molecule is substituted with a chlorine atom.

Next, the HCO-1230xa is subjected to two operations of hydrofluorination and dehydrochlorination to produce HFO-1234yf.

However, a photo-reaction is included in chlorination during production of the HCO-1230xa, and two by-products, HCO-1230xf ($CCl_3CCl=CH_2$) and HCO-1230zd ($CCl_3CH=CHCl$), are also produced in addition to the HCO-1230xa as products of final dehydrochlorination. Therefore, an additional process for converting the by-products into HCO-1230xa is required (see US Publication No. 2012/0022303). Accordingly, the HCO-1230xa is relatively expensive and is not readily distributed on a commercial scale since it is produced with complicated operations as described above.

(2) A method of substituting a hydrogen atom bound to carbon in the center of the molecule with a halogen atom after fluorination:

In this method, first, fluorination and dehydrochlorination of HCC-250fb are carried out to produce 3,3,3-trifluoropropene ($CF_3CH=CH_2$, HFO-1243zf), as represented by the following Scheme 4.

Scheme 4

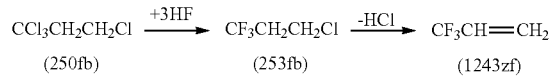

Next, the produced HFO-1243zf i) is subjected to chlorination, followed by hydrofluorination to produce HFO-1234yf, as represented by the following Scheme 5, or ii) is simultaneously subjected to chlorination/hydrofluorination (chlorofluorination) to produce HFO-1234yf, as represented by the following Scheme 6.

Scheme 5

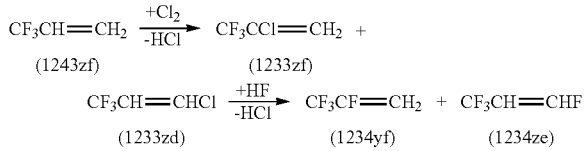

Scheme 6

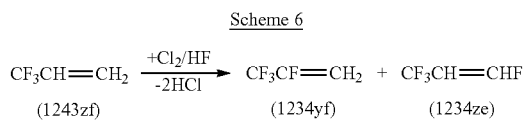

However, when the reaction is carried out as represented by Scheme 5 or 6, significant amounts of side reaction products such as 1233zd and 1234ze are produced. Therefore, a separate process for handling the 1233zd or 1234ze is required.

In summary, when HFO-1234yf is produced as a next-generation alternative refrigerant, a method of producing 1,1,1,2,3-pentafluoropropane ($CF_3CHFCH_2F$, HFC-245eb) as an intermediate has an advantage in that it can be used to produce HFO-1234yf simply and effectively, compared to the other methods. However, when HFP is used as a starting material to produce the HFC-245eb, this is not commercially viable due to its economic inefficiency. On the other hand, when a relatively inexpensive raw material, HCC-250fb, is used without undergoing a process for producing HFC-245eb, a multi-stage process is required. Also, since large amounts of by-products are produced by side reactions, a complicated process for handling the by-products is also required.

Meanwhile, there is a direct fluorination method of directly producing HFC-245eb through a direct reaction of HFO-1243zf with fluorine gas. In this case, however, carbon-carbon cleavage may take place due to high reactivity of the fluorine gas, and many by-products such as HFC-236ea ($CF_3CHFCHF_2$), HFC-236cb ($CF_3CF_2CH_2F$), HFC-227ea ($CF_3CHFCF_3$), HFC-227ca ($CF_3CF_2CHF_2$) and FC-218 ($CF_3CF_2CF_3$) may be produced. To carry out a fluorination reaction under milder conditions, a method of diluting fluorine gas with an excessive amount of nitrogen gas is known in the art. In this case, however, there are problems related to a localized fluorination reaction and a separation of low-boiling-point products and nitrogen. In particular, it is difficult to take a commercial approach to this method due to difficulty in handling non-reacted fluorine gases.

SUMMARY

Accordingly, example embodiments of the present invention are provided to substantially obviate one or more problems due to limitations and disadvantages of the related art.

Example embodiments of the present invention provide a method of producing HFC-245eb, which is an intermediate of HFO-1234yf, with high yield using 3,3,3-trifluoropropene ($CF_3CH=CH_2$, HFO-1243zf), which is produced from an inexpensive raw material, HCC-250fb, through fluorination and dehydrochlorination, as a starting material.

Example embodiments of the present invention also provide a method of continuously producing HFC-245eb from HFO-1243zf with high yield using an indirect fluorination method (i.e., mild fluorination) in which a cobalt fluoride ($CoF_2/CoF_3$) is used as a fluid catalyst.

In some example embodiments, a method of continuously producing 1,1,1,2,3-pentafluoropropane is provided. The method includes (a) bringing a $CoF_3$-containing cobalt fluoride into contact with 3,3,3-trifluoropropene in a reactor to produce a $CoF_2$-containing cobalt fluoride and 1,1,1,2,3-pentafluoropropane, (b) transferring the $CoF_2$-containing cobalt fluoride in the reactor to a regenerator and bringing the transferred $CoF_2$-containing cobalt fluoride into contact with fluorine gas to regenerate a $CoF_3$-containing cobalt fluoride, and (c) transferring the $CoF_3$-containing cobalt fluoride in the regenerator to the reactor and employing the transferred $CoF_3$-containing cobalt fluoride in Operation (a).

The contact of the $CoF_3$-containing cobalt fluoride with the 3,3,3-trifluoropropene in Operation (a), and the contact of the $CoF_2$-containing cobalt fluoride with the fluorine gas in Operation (b) may be carried out by countercurrent contact.

The reactor and the regenerator may comprise a rotary shaft having paddle-type blades attached thereto, and the cobalt fluorides in the reactor and the regenerator may be transferred by rotation of the rotary shaft. In addition, a transfer rate of the cobalt fluorides in the reactor and the regenerator may be adjusted by adjusting an angle of the paddle-type blades attached to the rotary shaft.

In Operation (a), a molar ratio between the $CoF_3$ in the $CoF_3$-containing cobalt fluoride and the 3,3,3-trifluoropropene may be in a range of 2:1 to 20:1.

Also in Operation (a), the $CoF_3$-containing cobalt fluoride may further include $CoF_2$ so that a molar ratio between $CoF_3$ and $CoF_2$ can fall within a range of greater than 20:0 to less than 2:18, based on 1 mole of the 3,3,3-trifluoropropene. In this case, the $CoF_2$ may be preferably included at such an amount that the number of moles of the $CoF_2$ is greater than the number of moles of the $CoF_3$ within the molar ratio between the $CoF_3$ and the $CoF_2$.

In Operation (b), a molar ratio between the $CoF_2$ in the $CoF_2$-containing cobalt fluoride and the fluorine gas may be in a range of 2:1 to 20:1.

Also in Operation (b), the $CoF_2$-containing cobalt fluoride may further include $CoF_3$ so that a molar ratio between $CoF_2$ and $CoF_3$ can fall within a range of greater than 20:0 to less than 2:18, based on 1 mole of the fluorine gas.

Meanwhile, in Operation (a), the $CoF_3$-containing cobalt fluoride may be used in a state of being diluted with a metal fluoride.

The transfer of the $CoF_2$-containing cobalt fluoride from the reactor to the regenerator may be carried out using a first screw conveyor coupled to the reactor and the regenerator so that an upward slope is formed from the reactor toward the regenerator. Also, the transfer of the $CoF_3$-containing cobalt fluoride from the regenerator to the reactor may be carried out using a second screw conveyor coupled to the regenerator and the reactor so that an upward slope is formed from the regenerator to the reactor.

In other example embodiments, an apparatus for continuously producing 1,1,1,2,3-pentafluoropropane is provided. The apparatus includes a reactor configured to bring a $CoF_3$-containing cobalt fluoride into countercurrent contact with 3,3,3-trifluoropropene to produce a $CoF_2$-containing cobalt fluoride and 1,1,1,2,3-pentafluoropropane, a first screw conveyor configured to draw the $CoF_2$-containing cobalt fluoride from the reactor, a regenerator configured to receive the $CoF_2$-containing cobalt fluoride from the first screw conveyor and bring the received $CoF_2$-containing cobalt fluoride into countercurrent contact with fluorine gas to regenerate a $CoF_3$-containing cobalt fluoride, and a second screw conveyor configured to draw the $CoF_3$-containing cobalt fluoride from the regenerator and transfer the $CoF_3$-containing cobalt fluoride to the reactor.

The reactor and the regenerator may comprise a rotary shaft having paddle-type blades attached thereto, and the cobalt fluorides in the reactor and the regenerator may be transferred by rotation of the rotary shaft. In addition, a transfer rate of the cobalt fluorides in the reactor and the regenerator may be adjusted by adjusting an angle of the paddle-type blades attached to the rotary shaft.

The first screw conveyor may be coupled to the reactor and the regenerator so that an upward slope is formed from the reactor to the regenerator. Also, the second screw conveyor may be coupled to the regenerator and the reactor so that an upward slope is formed from the regenerator to the reactor.

Also, the apparatus for continuously producing 1,1,1,2,3-pentafluoropropane may further include an electrostatic precipitator configured to receive 1,1,1,2,3-pentafluoropropane produced in the reactor and recover the $CoF_3$-containing cobalt fluoride that may be entrained with the received 1,1,1,2,3-pentafluoropropane.

BRIEF DESCRIPTION OF DRAWINGS

Example embodiments of the present invention will become more apparent by describing in detail example embodiments of the present invention with reference to the accompanying drawings, in which.

DESCRIPTION OF EXAMPLE EMBODIMENTS

Figure 1:
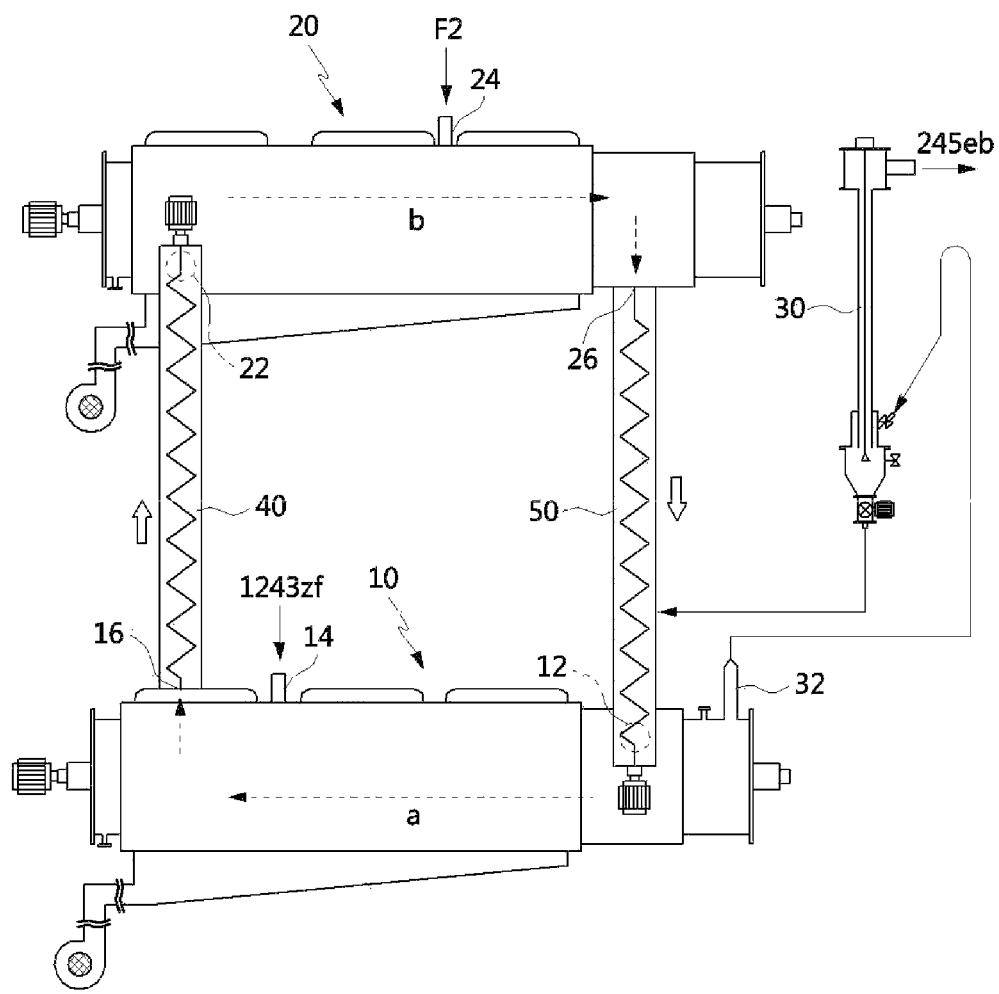
FIG. 1 is a schematic top view showing a continuous fluorination apparatus used to produce 1,1,1,2,3-pentafluoropropane according to one example embodiment of the present invention.

Example embodiments of the present invention are disclosed herein. However, specific structural and functional details disclosed herein are merely representative for purposes of describing example embodiments of the present invention. Example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should also be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

In the description of the present invention, the term "cobalt fluoride" means a substance including at least one of cobalt (II) fluoride ($CoF_2$) and cobalt(III) fluoride ($CoF_3$).

Also, it should be understood that the term "$CoF_2$-containing cobalt fluoride" means a cobalt fluoride including at least $CoF_2$ as an effective component, and the term "$CoF_3$-containing cobalt fluoride" means a cobalt fluoride including at least $CoF_3$ as an effective component. Therefore, this is not intended to exclude the $CoF_2$-containing cobalt fluoride from further including $CoF_3$, or the $CoF_3$-containing cobalt fluoride from further including $CoF_2$.

Also, the term "cobalt fluoride catalyst" or "catalyst" is used to have the same meaning as the cobalt fluoride including at least $CoF_3$.

A source gas or reactive gas is used with the same meaning as 3,3,3-trifluoropropene (HFO-1243zf), and a product gas is used with the same meaning as 1,1,1,2,3-pentafluoropropane (HFC-245eb).

The present invention relates to a method of continuously producing 1,1,1,2,3-pentafluoropropane through fluorination of 3,3,3-trifluoropropene using a cobalt fluoride as a fluid catalyst.

More particularly, the method includes (a) bringing a $CoF_3$-containing cobalt fluoride into contact with 3,3,3-trifluoropropene in a reactor to produce a $CoF_2$-containing cobalt fluoride and 1,1,1,2,3-pentafluoropropane, (b) transferring the $CoF_2$-containing cobalt fluoride in the reactor to a regenerator and bringing the transferred $CoF_2$-containing cobalt fluoride into contact with fluorine gas to regenerate a $CoF_3$-containing cobalt fluoride, and (c) transferring the $CoF_3$-containing cobalt fluoride in the regenerator to the reactor and employing the transferred $CoF_3$-containing cobalt fluoride in Operation (a).

Operations (a) to (c) may be referred to as a catalytic reaction process (a), a catalyst regeneration process (b), and a catalyst reuse process (c), respectively.

The processes may be continuously carried out, and the catalytic reaction process (a) and the catalyst regeneration process (b) may be represented by the following Scheme 7.

Scheme 7

Catalytic reaction process:

Catalytic regeneration process:

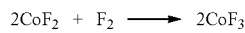

FIG. 1 is a schematic top view showing a continuous fluorination apparatus used to produce 1,1,1,2,3-pentafluoropropane according to one example embodiment of the present invention.

Hereinafter, the processes will be described in detail with reference to FIG. 1.

Catalytic Reaction Process

The catalytic reaction process is to bring a $CoF_3$-containing cobalt fluoride supplied in a solid phase into contact with 3,3,3-trifluoropropene (HFO-1243zf) supplied in a gas phase in a reactor 10 to produce 1,1,1,2,3-pentafluoropropane (HFC-245eb). For example, the reactor 10 may be formed in a tubular structure.

The $CoF_3$-containing cobalt fluoride and the 3,3,3-trifluoropropene are supplied through a $CoF_3$ supply port 12 and a source gas supply port 14, respectively, and may flow in opposite directions in the reactor 10 and be brought into countercurrent contact with each other.

According to one example embodiment, a rotary shaft having a plurality of paddle-type blades attached thereto is provided in the reactor 10, and the $CoF_3$-containing cobalt fluoride may be transferred in a predetermined direction (for example, a direction indicated by arrow a) by rotation of the rotary shaft. In this case, a transfer rate of the $CoF_3$-containing cobalt fluoride may be properly set by adjusting at least one of a rotation speed of the rotary shaft and an angle of the paddle-type blades. The paddle-type blades serve to transfer the $CoF_3$-containing cobalt fluoride while rotating the $CoF_3$-containing cobalt fluoride. Therefore, the paddle-type blades may be effectively used to stir a solid cobalt fluoride so as to facilitate the contact and heat transfer between the source gas and the solid cobalt fluoride.

In the reactor 10, the $CoF_3$ in the $CoF_3$-containing cobalt fluoride and the 3,3,3-trifluoropropene are subjected to the catalytic reaction represented by Scheme 7 to produce $CoF_2$ and 1,1,1,2,3-pentafluoropropane.

In this case, a molar ratio between the $CoF_3$ and the 3,3,3-trifluoropropene used in the catalytic reaction may be in a range of 2:1 to 20:1. In particular, the $CoF_3$ may be presented at an excessive molar amount exceeding a stoichiometric amount required for the catalytic reaction, based on the molar amount of the 3,3,3-trifluoropropene (i.e., the number of moles of the $CoF_3$ exceeding 2 moles based on 1 mole of the 3,3,3-trifluoropropene). In this case, when the $CoF_3$ is not regenerated to a desired extent due to insufficient supply of the fluorine gas in the regenerator 20 as will be described later, an extra $CoF_3$ may take part in the catalytic reaction in the reactor 10, thereby stably maintaining a conversion rate of the catalytic reaction (yield of a product gas). However, the $CoF_3$ may be preferably used at the number of moles of 20 moles or less with respect to 1 mole of the 3,3,3-trifluoropropene, in consideration of the economic feasibility and efficiency of the reaction.

Meanwhile, the $CoF_3$-containing cobalt fluoride used in the catalytic reaction may be composed only of $CoF_3$, but preferably may further include $CoF_2$ so that a molar ratio between the $CoF_3$ and the $CoF_2$ can fall within a range of greater than 20:0 to less than 2:18, based on 1 mole of the 3,3,3-trifluoropropene. When the fluorination of 3,3,3-trifluoropropene (HFO-1243zf) is carried out, many fluorides such as HFC-236ea ($CF_3CHFCHF_2$) HFC-236cb ($CF_3CF_2CH_2F$), HFC-227ea ($CF_3CHFCF_3$), HFC-227ca ($CF_3CF_2CHF_2$) and FC-218 ($CF_3CF_2CF_3$) may be produced as the by-products, in addition to the desired product gas, 1,1,1,2,3-pentafluoropropane (HFC-245eb). Among these, only the HFC-245eb is a compound produced by incorporating a fluorine atom into a double bond, and the others are compounds produced by substituting hydrogen with a fluorine atom. Since the conditions used to incorporate a fluorine atom into a double bond is milder than the conditions used to substitute hydrogen with a fluorine atom, a yield of the HFC-245eb may be maximized by properly adjusting a ratio between $CoF_3$ and $CoF_2$ in the catalyst.

That is, when the $CoF_3$-containing cobalt fluoride used in the catalytic reaction further include $CoF_2$, the $CoF_2$ may serve as a diluent with respect to a $CoF_3$ catalyst. Therefore, an excessive catalytic reaction of a reactive gas may be suppressed to reduce production of the by-products rather than the HFC-245eb. In particular, when the $CoF_3$-containing cobalt fluoride further including $CoF_2$ is supplied, the production of the by-products may be minimized by allowing the $CoF_2$ to be included at such an amount that the number of moles of the $CoF2$ is greater than the number of moles of the $CoF_3$.

Also, in order to obtain the effect according to dilution of the $CoF_3$ as described above, the $CoF_3$-containing cobalt fluoride used for the catalytic reaction may diluted with a separate diluent. Various kinds of metal fluorides may be used as the diluents. By way of example, the metal fluorides such as $CaF_2$ and $MnF_2$ which have similar fluidity to the cobalt fluoride may be used herein. A level of dilution may be set to 80% of the entire weight, and may be properly adjusted according to diluents used and reaction conditions.

Meanwhile, an electric heater is attached to an outer wall of the reactor 10 to supply heat required for the catalytic reaction to the reactor 10. A proper reaction temperature in the reactor 10 is in a range of 150 to 300° C., and the reaction temperature may be constantly maintained by providing cold air into a blower through a jacket installed outside the reactor 10.

The source gas (HFO-1243zf) is supplied to the reactor 10 at a pressure of 0.5 to 1 $kg/cm^2G$, preferably 0.2 to 0.4 $kg/cm^2G$.

The 1,1,1,2,3-pentafluoropropane produced in the reactor 10 is transferred in a direction opposite to a transfer direction of the $CoF_3$-containing cobalt fluoride, and discharged through a product gas discharge port 32 of the reactor 10. In this case, a cobalt fluoride catalyst having a diameter of 2 mm or less in a fine powdery shape may be entrained with the product gas, and then discharged. The discharged cobalt fluoride catalyst may be collected and recovered while passing through an electrostatic precipitator 30 coupled to the product gas discharge port 32 of the reactor 10.

Also, the $CoF_2$-containing cobalt fluoride produced as a result of the catalytic reaction is discharged through a $CoF_2$ discharge port 16 of the reactor 10, and transferred to the regenerator 20 through the first transfer unit 40.

Catalyst Regeneration Process

The catalyst regeneration process is to bring a $CoF_2$-containing cobalt fluoride supplied in a solid phase into contact with a fluorine gas supplied in a gas phase in the regenerator 20 to produce a $CoF_3$-containing cobalt fluoride. The regenerator 20 may be, for example, formed in a tubular structure.

The $CoF_2$-containing cobalt fluoride and the fluorine gas may be supplied through the $CoF_2$ supply port 22 and the fluorine gas supply port 24, respectively, and may flow in opposite directions in the regenerator 20 and be brought into countercurrent contact with each other.

According to one example embodiment, a rotary shaft having a plurality of paddle-type blades attached thereto is provided in the regenerator 20, and the $CoF_2$-containing cobalt fluoride may be transferred in a predetermined direction (for example, a direction indicated by arrow b) by rotation of the rotary shaft. In this case, a transfer rate of the $CoF_2$-containing cobalt fluoride may be properly set by adjusting at least one of a rotation speed of the rotary shaft and an angle of the paddle-type blades.

The paddle-type blades serve to transfer the $CoF_2$-containing cobalt fluoride while rotating the $CoF_2$-containing cobalt fluoride. Therefore, the paddle-type blades may be effectively used to stir a solid cobalt fluoride so as to facilitate the contact and heat transfer between the fluorine gas and the solid cobalt fluoride.

In the regenerator 20, the $CoF_2$ in the $CoF_2$-containing cobalt fluoride and the fluorine gas are subjected to the catalyst regeneration reaction represented by Scheme 7 to produce $CoF_3$.

In this case, a molar ratio between the $CoF_2$ and the fluorine gas may be in a range of 2:1 to 20:1. In particular, the $CoF_2$ may be present at an excessive molar amount exceeding a stoichiometric amount required for the catalyst regeneration reaction, based on the molar amount of the fluorine gas (i.e., the number of moles of the $CoF_2$ exceeding 2 moles based on 1 mole of the fluorine gas). In this case, although the fluorine gas is temporally supplied at a more excessive amount than a predetermined amount of the fluorine gas due to abnormal driving of the regenerator 20, an extra $CoF_2$ may react with the fluorine gas, thereby preventing production of a non-reacted fluorine gas. Also, as the fluorine gas does not sufficiently react with $CoF_2$ under normal driving of the regenerator 20, the non-reacted fluorine gas may be produced. In this case, since an extra $CoF_2$ reacts with the non-reacted fluorine gas, the fluorine gas may be prevented from moving to the reactor 10. However, the $CoF_2$ may be preferably used at the number of moles of 20 moles or less with respect to 1 mole of the fluorine gas, in consideration of the economic feasibility and efficiency of the reaction.

Meanwhile, the $CoF_2$-containing cobalt fluoride used for the catalyst regeneration reaction may be composed only of $CoF_2$, but preferably may further include $CoF_3$ so that a molar ratio between the $CoF_2$ and the $CoF_3$ can fall within a range of greater than 20:0 to less than 2:18, based on 1 mole of the fluorine gas. In this case, although the fluorine gas is supplied to the regenerator 20 at an insufficient amount compared to the predetermined amount of the fluorine gas, an extra $CoF_3$ may take part in the catalytic reaction in the reactor 10, thereby stably maintaining a conversion rate of the catalytic reaction (yield of a product gas).

An electric heater is attached to an outer wall of the regenerator 20 to supply heat required for the catalyst regeneration reaction to the regenerator 20. A proper reaction temperature is in a range of 250 to 350° C., and the reaction temperature may be constantly maintained by providing cold air into a blower through a jacket installed outside the regenerator 20.

The fluorine gas is supplied to the regenerator 20 at a pressure of 0.5 to 1 $kg/cm^2G$, preferably 0.2 to 0.4 $kg/cm^2G$.

Also, the $CoF_3$-containing cobalt fluoride regenerated in the catalyst regeneration reaction is discharged through the $CoF_3$ discharge port 26 of the regenerator 20, and then transferred to the reactor 10 through the second transfer unit 50.

Transfer Between Reactor and Regenerator

The $CoF_2$-containing cobalt fluoride discharged from the reactor 10 after the catalytic reaction process is transferred to the regenerator 20 through the first transfer unit 40, and the transferred $CoF_2$-containing cobalt fluoride is regenerated into a $CoF_3$-containing cobalt fluoride by a catalyst regeneration process.

Also, the $CoF_3$-containing cobalt fluoride regenerated in the regenerator 20 is transferred to the reactor 10 through the second transfer unit 50, and the transferred $CoF_3$-containing cobalt fluoride is subjected to a catalytic reaction process to produce a $CoF_2$-containing cobalt fluoride and a product gas (HFC-245eb).

That is, the first and second transfer units 40 and 50 serve to circulate the cobalt fluorides, which are used for the catalytic reaction process and the catalyst regeneration process, between the reactor 10 and the regenerator 20.

According to one example embodiment, the first and second transfer units 40 and 50 may be screw conveyors, each of which has screws formed therein.

More particularly, the transfer of the $CoF_2$-containing cobalt fluoride from the reactor 10 to the regenerator 20 may be carried out using the first screw conveyor 40 coupled to the reactor 10 and the regenerator 20 so that an upward slope is formed from the reactor 10 toward the regenerator 20. Also, the transfer of the $CoF_3$-containing cobalt fluoride from the regenerator 20 to the reactor 10 may be carried out using the second screw conveyor 50 coupled to the regenerator 20 and the reactor 10 so that an upward slope is formed from the regenerator 20 toward the reactor 10.

Figure 2:
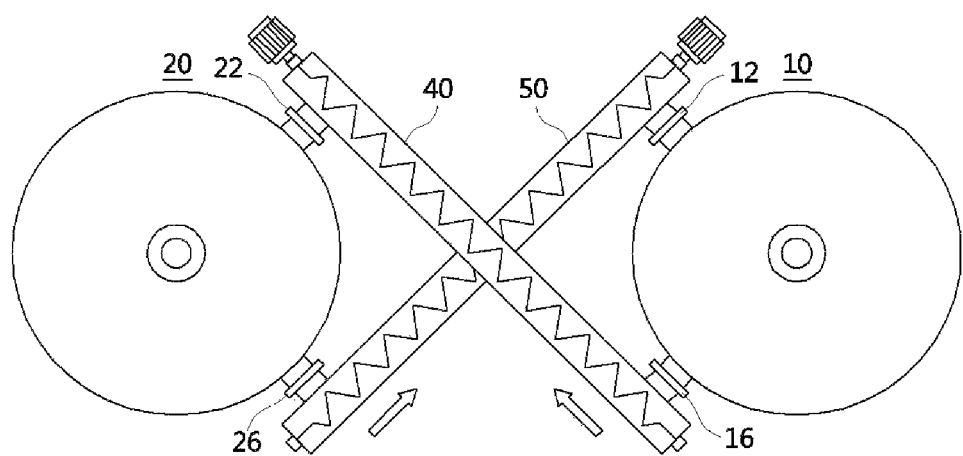
FIG. 2 is a schematic side view showing the continuous fluorination apparatus according to one example embodiment of the present invention.

FIG. 2 is a schematic side view showing the continuous fluorination apparatus according to one example embodiment of the present invention.

Referring to FIG. 2, the first screw conveyor 40 is coupled in an upward slope so that the $CoF_2$ can be transferred from the $CoF_2$ discharge port 16 disposed at a lower portion of the reactor 10 to the $CoF_2$ supply port 22 disposed at an upper portion of the regenerator 20. Also, the second screw conveyor 50 is coupled in an upward slope so that the $CoF_3$ can be transferred from the $CoF_3$ discharge port 26 disposed at a lower portion of the regenerator 20 to the $CoF_3$ supply port 12 disposed at an upper portion of the reactor 10. Inclination angles of the first and second screw conveyors 40 and 50 may be in a range of 20° to 90°.

The first and second screw conveyors 40 and 50 may be installed in an upper slope to transfer the cobalt fluoride, and thus the first and second screw conveyors 40 and 50 may transfer the cobalt fluoride while being filled with no empty space therein. Therefore, it is possible to effectively prevent the reactive gas from moving to the regenerator 20 through the first screw conveyor 40, or prevent the fluorine gas from moving to the reactor 10 through the second screw conveyor 50.

Meanwhile, since a catalyst reaction temperature in the reactor 10 may be lower than a catalyst regeneration temperature in the regenerator 20, the first screw conveyor 40 may serve to increase a temperature of the $CoF_2$-containing cobalt fluoride transferred using an external electric heater, and the second screw conveyor 50 may serve to decrease a temperature of the $CoF_3$-containing cobalt fluoride transferred by allowing cooling water to flow in an external jacket.

Compositions of Cobalt Fluoride

As described above with reference to the catalytic reaction process and the catalyst regeneration process, according to one example embodiment, the compositions of the cobalt fluoride flowing between the reactor 10 and the regenerator 20 may be realized in a state in which $CoF_2$ and $CoF_3$ co-exist at a predetermined ratio.

The following Table 1 lists one example embodiment of a cobalt fluoride whose compositions are run at a predetermined composition ratio in the reactor 10 and the regenerator 20.

TABLE 1

| Fluorine gas | Source gas | Compositions of cobalt fluoride supplied to regenerator (after catalytic reaction and before beginning of catalyst regeneration) | Compositions of cobalt fluoride supplied to reactor (after catalyst regeneration and before beginning of catalytic reaction) |
|---|---|---|---|
| 10 mole/hr | 10 mole/hr | $CoF_3$ 10 to 30 mole/hr $CoF_2$ 90 to 70 mole/hr | $CoF_3$ 30 to 50 mole/hr $CoF_2$ 70 to 50 mole/hr |
| 10 mole/hr | 10 mole/hr | $CoF_3$ 10 to 30 mole/hr $CoF_2$ 190 to 170 mole/hr | $CoF_3$ 30 to 50 mole/hr $CoF_2$ 170 to 150 mole/hr |

As listed in Table 1, when the cobalt fluoride flows under a condition in which $CoF_2$ is present at a more excessive amount than $CoF_3$ while maintaining the entire amount of the cobalt fluoride at a more excessive amount than the fluorine gas and the source gas, the following effects may be obtained.

(1) A non-reacted fluorine gas which does not sufficiently react in the regenerator 20 may sufficiently react with an extra $CoF_2$ to prevent the non-reacted fluorine gas from moving to the reactor 10, (2) A fluorine gas may sufficiently react with an extra $CoF_2$ to prevent production of a non-reacted fluorine gas even when an excessive amount of the fluorine gas is supplied to the regenerator 20 at once due to abnormal supply of the fluorine gas, (3) A yield of the product gas may be constantly maintained since an extra $CoF_3$, which has been present at an excessive amount in the reactor compared with that of the source gas, may react with the reactive gas in the reactor even when a small amount of the fluorine gas is supplied to the regenerator 20 due to abnormal supply of the fluorine gas, and (4) Particularly, production of perfluorides such as HFC-236ea ($CF_3CHFCHF_2$) HFC-236cb ($CF_3CF_2CH_2F$), HFC-227ea ($CF_3CHFCF_3$), HFC-227ca ($CF_3CF_2CHF_2$) and FC-218 ($CF_3CF_2CF_3$) may be suppressed when a reaction is carried out while an excessive amount of $CoF_2$ flows compared with that of $CoF_3$.

Therefore, according to example embodiments of the present invention, the optimum conversion rate from HFO-1243zf to HFC-245eb and the selectivity may be readily adjusted by adjusting a ratio of the source gas and fluorine gas to the cobalt fluoride or a ratio between $CoF_3$ and $CoF_2$ at a constant reaction temperature.

Hereinafter, preferred Experimental Examples are provided to facilitate better understanding of the present invention. However, the following Experimental Examples are intended to facilitate better understanding of the present invention, but are not intended to limit the Experimental Examples of the present invention.

Preparation of Reaction System

A reaction system was prepared, as shown in FIG. 1.

Each of a reactor and a regenerator was provided with a shaft (with a diameter of 10 cm) rotating at a constant rate in a stainless steel tube (with a diameter of 30 cm and a length of 250 cm), and a cobalt fluoride was moved forward at a constant rate by adjusting an angle of paddle-type blades attached to the shaft. The paddle-type blades attached to the shaft were welded in a state in which a tube having a diameter of 3.8 cm was fit through the shaft, and paddles were alternately installed with respect to each other. The blades attached to the paddles had a rectangular shape so that a powdery solid cobalt fluoride could be readily spread. Also, the blades might move with being fit into an end of a paddle tube, and be fixed with bolts to adjust a desired angle of the blades.

Since a retention amount of the cobalt fluoride varied according to the flow velocity, the cobalt fluoride was filled respectively in the reactor and the regenerator at a charge amount of 24 to 48 kg so that the a charge amount of the cobalt fluoride reached 20 to 40% (% by bulk volume) of the volume of each of the reactor and the regenerator. Rotation speeds of shafts of the reactor and the regenerator were fixed at 9.4 RPM, and the angle of the blades attached to the paddles was adjusted and set so that the flow velocity of the cobalt fluoride reached 48 to 96 kg/hr, depending on an amount of the cobalt fluoride.

A bow-shaped electric heater was installed outside the reactor and the regenerator to supply heat required for the catalytic reaction and catalyst regeneration reaction, and the heat generated during a catalytic reaction process and a catalyst regeneration process was cooled by supplying cold air from a lower portion to an upper portion through a jacket installed outside the electric heater so as to maintain a constant temperature.

The first screw conveyor was installed so that a tube having a diameter of 10 cm was formed aslant at an angle of approximately 30° from a lower portion of a rear stage of the reactor (a portion of the rear stage through which the cobalt fluoride undergoing the catalytic reaction is transferred, the same as above) to an upper portion of a front stage of the regenerator (a portion of the front stage through which the cobalt fluoride starts to flow for the catalyst regeneration reaction, the same as above). The second screw conveyor was installed so that a tube having a diameter of 10 cm was formed aslant at an angle of approximately 30° from a lower portion of a rear stage of the regenerator (a portion of the rear stage through which the cobalt fluoride undergoing the catalyst regeneration reaction is transferred, the same as above) to an upper portion of a front stage of the reactor (a portion of the front stage through which the cobalt fluoride starts to flow for the catalytic reaction, the same as above). The first and second screw conveyors transferred the catalyst in an upward direction due to the presence of internal screws, and a maximum transfer rate was set to 120 kg/hr.

A rotation speed of the screws was 50 rpm in maximum, and an inverter was used to adjust alternating current frequencies, thereby adjusting a transfer rate. The first screw conveyor used an external electric heater to increase a temperature while transferring the cobalt fluoride in the reactor to the regenerator, and the second screw conveyor allowed cooling water to flow through an external jacket to decrease a temperature while transferring the cobalt fluoride in the regenerator to the reactor.

The product (HFC-245eb) produced in the reactor was discharged through the front-stage discharge port of the reactor, and the entrained cobalt fluoride catalyst was collected using an electrostatic precipitator. The cobalt fluoride attached to an electrostatic precipitator was detached by periodically applying vibrations to the electrostatic precipitator, and then transferred to the first screw conveyor. The catalyst-free product was compressed and stored to calculate a yield and compositions of the product.

Preparation of Reaction

Only the first screw conveyor was disassembled, and 96 kg of $CoF_2$ was added through a $CoF_2$ supply port (an output of the first screw conveyor) provided at an upper portion of the front stage of the regenerator while rotating the second screw conveyor and the paddle shafts of the reactor and the regenerator. A flow rate of $CoF_2$ discharged through an input of the first screw conveyor provided at a lower portion of the rear stage of the reactor was measured according to the angle of the blades attached to the paddles. At the same time, the alternating current frequency was adjusted using an inverter according to the transfer rate of $CoF_2$, thereby adjusting the number of rotations of the screws of the second screw conveyor. When the angle of the paddle-type blades and the number of rotations of the screws were determined according to the transfer rate of $CoF_2$, the $CoF_2$ was completely discharged. Thereafter, the first screw conveyor was assembled, and a catalyst was added through an inspection hole of the rear stage of the regenerator while rotating the screws of the conveyors and the paddle shafts of the reactor and the regenerator. Then, moisture in the catalyst was completely removed while allowing nitrogen to flow at a flow rate of 2 L/min to 15 L/min through a source gas input of the reactor (a point of approximately ⅔ apart from the front stage of the reactor) as temperatures of heaters of the reactor and the regenerator were gradually increased to 350° C. In this case, the electrostatic precipitator was run.

Experimental Examples 1 to 9

A total of 48 kg of $CoF_2$ was added into the reactor and the regenerator, the angle of the blades attached to the paddles was adjusted, and the number of rotations of the screws of each conveyor was adjusted so that a transfer rate of $CoF_2$ reached 48 kg/hr. Thereafter, internal temperatures of the reactor and the regenerator were increased by allowing nitrogen to flow in the reactor and the regenerator (flow rate of 2 L/min to 15 L/min), thereby removing moisture in $CoF_2$. When the moisture in $CoF_2$ was completely removed, the internal temperatures of the reactor and the regenerator were maintained respectively to a temperature of 250° C. while gradually decreasing a flow rate of nitrogen to 2 L/min. First, a fluorine gas was added to the regenerator at a rate of 0.94 kg/hr for 3 hours, and the addition of the fluorine gas was then suspended. A catalyst was rotated for 1 hour, the fluorine gas was added again at a rate of 0.94 kg/hr for 30 minutes, and the source gas, HFO-1243zf ($CF_3CH=CH_2$), was added to the reactor at a rate of 2.45 kg/hr. A fluorination temperature of the regenerator was constantly maintained at 250° C. An initial molar ratio between $CoF_3$ and $CoF_2$ was adjusted by changing an addition time (3 hours, 2 hours and 1 hour) of an initial fluorine gas without adding the source gas (1243zf) when $CoF_2$ was filled to 100%. When the change in initial molar ratio between $CoF_3$ and $CoF_2$ (3/7→2/8→1/9) and the change in operation conditions were performed, HFP ($CF_3CF=CF_3$) was added to completely convert $CoF_3$ into $CoF_2$ and a reaction system was purged with nitrogen, and thus the changes were carried out under a condition in which $CoF_2$ was filled to 100% at the beginning.

Table 2 lists ratios of products at a cobalt fluoride flow rate of 48 kg/hr according to changes in reaction temperature of the reactor and composition ratio of initial $CoF_3/CoF_2$, as analyzed using GC.

TABLE 2

| Experimental Example | Initial $CoF_3/CoF_2$ molar ratio | $CoF_3/CoF_2$/1243zf molar ratio in reactor before reaction | Reactor (° C.) | 1243zf | 245eb | 236ea | 236cb | 227ea | 227ca | 218 | $CF_4$ |
|---|---|---|---|---|---|---|---|---|---|---|---|
| 1 | 3/7 | 5/5/1 | 250 | 0.2 | 70.5 | 17.2 | 5.5 | 2.1 | 3.2 | 0.6 | 0.2 |
| 2 | | | 200 | 12.8 | 69.7 | 11.1 | 1.3 | 1.1 | 1.3 | 0.3 | 0.1 |
| 3 | | | 150 | 39.5 | 47.8 | 6.7 | 2.2 | 0.7 | 1.4 | 0.2 | — |
| 4 | 2/8 | 4/6/1 | 250 | 2.8 | 77.2 | 13.2 | 3.3 | 1.4 | 0.9 | 0.5 | 0.1 |
| 5 | | | 200 | 18.4 | 70.0 | 7.7 | 1.6 | 0.7 | 0.8 | 0.2 | 0.1 |
| 6 | | | 150 | 40.8 | 46.7 | 6.5 | 2.2 | 0.7 | 0.9 | 0.2 | — |
| 7 | 1/9 | 3/7/1 | 250 | 4.5 | 81.2 | 7.3 | 1.8 | 1.2 | 0.9 | 0.4 | — |
| 8 | | | 200 | 19.3 | 71.0 | 6.4 | 1.4 | 0.6 | 0.4 | 0.2 | — |
| 9 | | | 150 | 49.5 | 44.9 | 4.1 | 0.8 | 0.4 | 0.1 | 0.1 | — |

As listed in Table 2, it could be seen that a ratio of the produced 1,1,1,2,3-pentafluoropropane (HFC-245eb) was increased at the same reaction temperature with a decrease in molar ratio between $CoF_3$ and $CoF_2$. Also, it could be seen that a ratio of the produced HFC-245eb was increased at the same molar ratio between $CoF_3$ and $CoF_2$ with an increase in reaction temperature.

Experimental Examples 10 to 13

Experimental Examples 10 to 13 were carried out in the same manner as in Experimental Examples 1 to 9, except that a total of 96 kg of $CoF_2$ was added to each of the reactor and the regenerator.

The following Table 3 lists ratios of products at a cobalt fluoride flow rate of 96 kg/hr according to changes in reaction temperature of the reactor and composition ratio of initial $CoF_3/CoF_2$, as analyzed using GC.

TABLE 3

| Experimental Example | Initial $CoF_3/CoF_2$ molar ratio | $CoF_3/CoF_2/1243zf$ molar ratio in reactor before reaction | Reactor (°C.) | 1243zf | 245eb | 236ea | 236cb | 227ea | 227ca | 218 | $CF_4$ |
|---|---|---|---|---|---|---|---|---|---|---|---|
| 10 | 3/17 | 5/15/1 | 300 | — | 85.3 | 6.5 | 5.5 | 1.3 | 1.3 | — | 0.2 |
| 12 | | | 250 | 2.5 | 91.3 | 2.4 | 2.1 | — | — | — | — |
| 13 | | | 200 | 15.2 | 84.2 | 0.2 | 0.2 | — | — | — | — |

As listed in Table 3, it could be seen that the 245eb had a high yield of 80% or more, which exceeded those of Experimental Examples 1 to 9, at all the reaction temperatures compared with those listed in Table 2 (1 mole of a source gas: 10 moles of $CoF_3/CoF_2$-containing cobalt fluoride). Also, the entire amount of the catalyst was decreased, based on 1 mole of the source gas (1243zf), but the molar ratio between $CoF_3$ and $CoF_2$ was decreased, compared with those of Experimental Examples 1 to 9. As a result, it could be seen that the selectivity to 245eb was shown to be very excellent.

Experimental Examples 14 to 16

The following Table 4 lists the results obtained by carrying out the reactions under the condition in which $CoF_3$ was present at an excessive amount compared with $CoF_2$ (Experimental Examples 14 and 15), and the condition in which pure $CoF_2$ was used in a regenerator (Experimental Example 16).

TABLE 4

| Experimental Example | Initial $CoF_3/CoF_2$ molar ratio | $CoF_3/CoF_2/1243zf$ molar ratio in reactor before reaction | Reactor (°C.) | 1243zf | 245eb | 236ea | 236cb | 227ea | 227ca | 218 | $CF_4$ |
|---|---|---|---|---|---|---|---|---|---|---|---|
| 14 | 18/2 | 20/0/1 | 150 | 6.5 | 32.5 | 16.5 | 15.5 | 12.3 | 10.2 | 4.5 | 1.2 |
| 15 | 8/2 | 10/0/1 | 150 | 10.4 | 43.2 | 11.1 | 12.3 | 9.3 | 8.2 | 4.0 | 1.0 |
| 16 | 0/20 | 2/18/1 | 350 | 8.5 | 87.3 | 2.2 | 1.9 | — | — | — | — |

As listed in Table 4, it could be seen that the HFC-245eb was obtained at a relatively higher yield than that of the by-products, perfluorides, even when $CoF_3$ was used at an excessive amount compared with that of $CoF_2$ (Experimental Examples 14 and 15). In this case, however, it could be seen that the selectivity of the HFC-245eb was lowered since a large amount of the perfluorides was formed due to a rapid exothermic reaction between the $CoF_3$ and the source gas (1243zf) even at a low reaction temperature. In particular, the conditions in which the pure $CoF_3$ was used in a reactor corresponded to conditions in which all the initial $CoF_2$ ($CoF_2$ in the regenerator) was converted into $CoF_3$ by a fluorination reaction. When an unreacted fluorine gas was present in the regenerator under such operation conditions, there was a potential risk of forcing the fluorine gas to flow into the reactor during movement of the $CoF_3$ from the regenerator to the reactor. Therefore, setting the operation conditions so that the cobalt fluoride further including the $CoF_2$ was used in the reactor instead of the cobalt fluoride composed of only the $CoF_3$ might be desirable to minimize the potential risk and improve the selectivity of the HFC-245eb.

As suggested in Experimental Example 16, when the reaction was carried out under conditions in which the $CoF_2$ was present at a more excessive amount than the $CoF_3$, it was possible to realize excellent selectivity to the HFC-245eb, which was substantially similar to the results of Experimental Examples 10 to 13. However, the conditions in which the pure $CoF_2$ was used in the regenerator corresponded to conditions in which all the $CoF_3$ in the reactor was converted into $CoF_2$ by a reaction with the source gas. When an unreacted source gas was present in the reactor under such operation conditions, there was a potential risk of forcing the source gas to flow into the regenerator during movement of the $CoF_2$ from the reactor to the regenerator. Therefore, setting the operation conditions so that the cobalt fluoride further including the $CoF_3$ was used in the regenerator instead of the cobalt fluoride composed of only the pure $CoF_2$ was more desirable.

Experimental Examples 17 and 18

The following Table 5 lists the results obtained by adding a metal fluoride as a diluent for cobalt fluorides and carrying out the reactions. The metal fluoride was added at a content of 20 to 40% by volume, based on the sum of the volumes of the reactor and the regenerator.

TABLE 5

| Experimental Example | Initial $CoF_3/CoF_2$ molar ratio | $CoF_3/CoF_2/1243zf$ molar ratio in reactor before reaction | Metal fluoride | Reactor (°C.) | 1243zf | 245eb | 236ea | 236cb | 227ea | 227ca | 218 | $CF_4$ |
|---|---|---|---|---|---|---|---|---|---|---|---|---|
| 17 | 3/3 | 5/1/1 | $CaF_2$ | 250 | 2.7 | 89.1 | 4.5 | 3.5 | — | — | — | — |
| 18 | 3/3 | 5/1/1 | $MnF_2$ | 250 | 2.1 | 90.4 | 5.4 | 2.1 | — | — | — | — |

Referring to Table 5, it could be seen that the HFC-245eb was obtained at a very high yield even when the $CoF_3$ in the reactor was used at an excessive amount compared with the $CoF_2$. The selectivity to the HFC-245 was comparable with the results of Experimental Examples 10 to 13 in which the inactive $CoF_2$ for the source gas was used at an excessive amount compare with the $CoF_3$. This was because the metal fluoride served as a diluent for $CoF_3$ to suppress rapid generation of heat caused by a reaction between the excess $CoF_3$ and the source gas (1243zf).

According to the present invention, 1,1,1,2,3-pentafluoropropane can be continuously produced with high yield from 3,3,3-trifluoropropene using a cobalt fluoride ($CoF_2$/$CoF_3$) as a fluid catalyst. Also, the reaction stability can be improved and the optimum conversion rate and selectivity can be readily adjusted by adjusting a ratio between 3,3,3-trifluoropropene or fluorine gas and a cobalt fluoride and a ratio between $CoF_2$ and $CoF_3$ in the cobalt fluoride.

While the example embodiments of the present invention and their advantages have been described in detail, it should be understood that various changes, substitutions and alterations may be made herein without departing from the scope of the invention.

What is claimed is:

1. A method of continuously producing 1,1,1,2,3-pentafluoropropane, comprising:
   (a) bringing a $CoF_3$-containing cobalt fluoride into a reactor to contact with 3,3,3-trifluoropropene to produce a $CoF_2$-containing cobalt fluoride and 1,1,1,2,3-pentafluoropropane;
   (b) transferring the $CoF_2$-containing cobalt fluoride in the reactor to a regenerator and bringing the transferred $CoF_2$-containing cobalt fluoride into contact with fluorine gas to regenerate a $CoF_3$-containing cobalt fluoride; and
   (c) transferring the $CoF_3$-containing cobalt fluoride in the regenerator to the reactor and employing the transferred $CoF_3$-containing cobalt fluoride in Operation (a),
   wherein, in Operation (a), the $CoF_3$-containing cobalt fluoride further includes $CoF_2$ and number of moles of the $CoF_2$ is greater than the number of moles of the $CoF_3$.

2. The method of claim 1, wherein the contact of the $CoF_3$-containing cobalt fluoride with the 3,3,3-trifluoropropene in Operation (a) and the contact of the $CoF_2$-containing cobalt fluoride with the fluorine gas in Operation (b) are carried out by countercurrent contact.

3. The method of claim 1, wherein the reactor and the regenerator comprise a rotary shaft having paddle-type blades attached thereto, and the cobalt fluorides in the reactor and the regenerator are transferred by rotation of the rotary shaft.

4. The method of claim 3, wherein a transfer rate of the cobalt fluorides in the reactor and the regenerator is adjusted by adjusting an angle of the paddle-type blades attached to the rotary shaft.

5. The method of claim 1, wherein, in Operation (a), a molar ratio between the $CoF_3$ in the $CoF_3$-containing cobalt fluoride and the 3,3,3-trifluoropropene is in a range of 2:1 to 20:1.

6. The method of claim 1, wherein, in Operation (a), the molar ratio between $CoF_3$ and $CoF_2$ falls within a range of less than 2:18, based on 1 mole of the 3,3,3-trifluoropropene.

7. The method of claim 1, wherein, in Operation (b), a molar ratio between the $CoF_2$ in the $CoF_2$-containing cobalt fluoride and the fluorine gas is in a range of 2:1 to 20:1.

8. The method of claim 1, wherein, in Operation (b), the $CoF_2$-containing cobalt fluoride further includes $CoF_3$ so that a molar ratio between $CoF_2$ and $CoF_3$ falls within a range of greater than 20:0 to less than 2:18, based on 1 mole of the fluoride gas.

9. The method of claim 1, wherein, in Operation (a), the $CoF_3$-containing cobalt fluoride is used in a state of being diluted with a metal fluoride.

10. The method of claim 1, wherein the transfer of the $CoF_2$-containing cobalt fluoride from the reactor to the regenerator is carried out using a first screw conveyor coupled to the reactor and the regenerator so that an upward slope is formed from the reactor toward the regenerator.

11. The method of claim 1, wherein the transfer of the $CoF_3$-containing cobalt fluoride from the regenerator to the reactor is carried out using a second screw conveyor coupled to the regenerator and the reactor so that an upward slope is formed from the regenerator to the reactor.

* * * * *